United States Patent [19]

Kaufman

[11] 4,279,922

[45] Jul. 21, 1981

[54] PHOTOSENSITIZING BENZOFURANACRYLICS

[75] Inventor: Kurt D. Kaufman, Kalamazoo, Mich.

[73] Assignee: Thomas C. Elder, Inc., Hamilton, Ind.

[21] Appl. No.: 173,438

[22] Filed: Jul. 29, 1980

[51] Int. Cl.³ .................... A61K 31/34; C07D 307/79
[52] U.S. Cl. .............................. 424/285; 260/346.22
[58] Field of Search .................... 260/346.22; 424/285

[56] References Cited

U.S. PATENT DOCUMENTS

| | | | |
|---|---|---|---|
| 3,201,421 | 8/1965 | Kaufman | 568/766 |
| 4,124,598 | 11/1978 | Hearst et al. | 260/343.21 |

OTHER PUBLICATIONS

MacLeod et al., Tet. Letters, No. 3, pp. 237–240, (1972).

*Primary Examiner*—Henry R. Jiles
*Assistant Examiner*—Bernard Dentz
*Attorney, Agent, or Firm*—Gordon W. Hueschen

[57] ABSTRACT

The invention relates to 5-benzofuranacrylic acid compounds, preferably loweralkyl-substituted in the benzofuran ring system, which have photosensitizing activity, especially oral and topical activity, as well as low toxicity.

20 Claims, No Drawings

PHOTOSENSITIZING BENZOFURANACRYLICS

BACKGROUND OF THE INVENTION

1. Field of Invention

Photochemotherapy, compounds having enhanced photosensitizing activity for use in photochemotherapy, benzofuranacrylic acid compounds.

2. Prior Art

Psoralens have been used for years as dermal photosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose is at least partially related to its ability to produce erythema upon the skin upon irradiation. Psoralens also have other uses, and their uses, as well as underlying rationale and theory, are partially elucidated in U.S. Pat. No. 4,124,598, and are otherwise well-known in the art from various preexisting publications.

With the increasing emphasis on photochemotherapeutic treatments for various purposes using psoralens and controlled application of ultraviolet light, the requirements for optimally-effective photosensitizing compounds have become more apparent. To eliminate the necessity of excessive and perhaps dangerous ultraviolet light applications or dosages, maximum photosensitization is one obvious criterion. However, to eliminate excessive periods of waiting before photochemotherapy can be commenced, rapid onset of photosensitization upon topical or oral administration of the photosensitizing agent is also of significance. Long or extended action is another criterion of significance in some cases, as when irradiation cannot be applied without some period of delay. Thus, the criteria of rapid onset, early maximization, and extended period of photosensitization action or effect are established as desirable criteria for the photosensitizing agent in this relatively new but rapidly-expanding field of photochemotherapy, certainly of equal importance as contrasted to the single previously-important criterion of high maximum photosensitization activity alone.

The recently-developed 4'-aminomethyl-4',5',8-trimethylpsoralen appears to be characterized by a high order of oral photosensitizing activity, but exhibits a high degree of toxicity. A low toxicity is, of course, essential. The compounds 5'-aminomethyl-4'-methylpsoralen and 8-aminomethylpsoralen, on the other hand, are essentially inactive orally, apparently due to absence of the 4-methyl group, thus making the photosensitizing activity even more unpredictable than ever in the area and immediate vicinity of the present invention. Benzofuranacrylic compounds of the present invention exhibit a wide range of activity and utility, and have heretofore, to the best of my knowledge, not been conceived or suggested, much less for a photosensitizing use or activity.

OBJECTS OF THE INVENTION

It is an object of the invention to provide novel benzofuranacrylic compounds. It is a further object to provide novel benzofuranacrylic compounds which exhibit photosensitizing activity or characteristics. It is an additional object to provide novel benzofuranacrylic compounds having enhanced photosensitizing characteristics in accord with the foregoing stated criteria. It is a still further object to provide novel benzofuranacrylic compounds having photosensitizing characteristics and relatively low toxicity, and of a structure differing essentially from known photosensitizing compounds, the properties of which could not be predicted on a basis of any known structure-activity relationships. Still other objects will be apparent to one skilled in the art and still additional objects will become apparent hereinafter from the following description and claims.

SUMMARY OF THE INVENTION

The present invention relates to benzofuranacrylic compounds having photosensitizing activity, especially oral activity, including early onset, increased maximum, and extended duration of activity, as well as low toxicity. When compared with known photosensitizing compounds of different structure, despite their different structure, the compounds are characterized by enhanced photosensitization properties according to the aforesaid various criteria, as well as relatively low toxicity. The invention is particularly concerned with various loweralkyl-substituted-6-loweralkanoyloxy-5-benzofuranacrylic acid, salts, and esters thereof, and especially such compounds wherein the loweralkyl substitution is methyl at a position selected from the beta, 2, 3, and 7 positions, and the basic structure is that of 6-acetoxy-5-benzofuranacrylic acid.

The compounds of the present invention have the formula

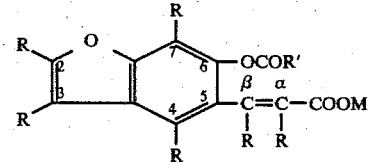

wherein R in each position is independently selected from the group consisting of hydrogen and loweralkyl, preferably methyl, wherein R' is loweralkyl, preferably methyl, and wherein M is selected from the group consisting of hydrogen, loweralkyl(R), and an alkali or alkaline earth metal, e.g., sodium, potassium, and calcium, preferably hydrogen. The symbols R' and the R at position 7 are preferably methyl. At least one of the R groups at positions 2 and 3 is preferably hydrogen but, if one or more are loweralkyl, they are preferably methyl. The R group at positions α, 4 and M is always preferably hydrogen.

The compounds of the invention may also be described as being selected from the group consisting of (a) alpha-R-beta-R-2-R-3-R-4-R-7-R-6-loweralkanoyloxy-5-benzofuranacrylic acid, wherein R in each of the stated positions is independently selected from hydrogen and loweralkyl, (b) alkali and alkaline earth metal salts thereof, and (c) loweralkyl esters thereof, preferably as an alpha-R-beta-R-2-R-3-R-4-R-7-R-6-loweralkanoyloxy-5-benzofuranacrylic acid, wherein R in each of the stated positions is independently selected from hydrogen and loweralkyl, more preferably as an alpha-R-beta-R-2-R-3-R-4-R-7-R-6-acetoxy-5-benzofuranacrylic acid, wherein R in each of the stated positions is independently selected from hydrogen and methyl, and especially as a beta-R-2-R-3-R-7-R-6-acetoxy-5-benzofuranacrylic acid, wherein R in each of the stated positions is independently selected from hydrogen and methyl, at least one of said 2, 3, and 7 R substituents being methyl.

DETAILED DESCRIPTION OF THE INVENTION

Starting materials for preparation of the compounds of the present invention are known. The starting psoralens usually have loweralkyl groups attached to one or more carbon atoms of the psoralen nucleus, such as positions 3, 4, 5, 4', 5', 8, and various combinations of the same. The compound 4,5',8-trimethylpsoralen is a well-known compound generically known as trisoralen. Various 4'-loweralkyl psoralens may be prepared according to the MacLeod adaptation of the straightforward Williamson ether synthesis. (MacLeod and Worth, Tetrahedron Letters 1972, 237–240). The various 4'-loweralkyl psoralens prepared by this method are the 4'-methyl-4-propylpsoralen, the 4',8-dimethylpsoralen, the 4,4',8-trimethylpsoralen, the 4,4'-dimethylpsoralen, the 3,4,4'-trimethylpsoralen, the 4'-methylpsoralen, and others. An abundance of loweralkyl psoralens utilizable as starting materials according to the present invention are accordingly known. The products of the present invention are prepared from these readily-available starting materials by the process of opening the pyrone ring by mild hydrolysis and esterification of the intermediate 6 hydroxy group with usual esterifying agents to produce an ester at the 6 position and a free acrylic acid radical at the 5 position of the benzofuran ring system. Subsequent esterification of the product produces a 5-esterified acrylic acid product. On the other hand, treatment with a base, such as sodium or potassium or calcium hydroxide, is productive of a salt of the acid. This salt-formation must be under controlled conditions inasmuch as, at elevated temperatures, mild alkaline hydrolysis of the ester group in 6 position when present in combination with a free acid radical at the 5 position, can be employed to cause the acid to revert into a ring-closed product which is generally identical with the starting material. The structure of the final product involved, the 5-benzofuranacrylic acid product, is generally confirmed by nuclear magnetic resonance spectra, using a Perkin Elmer Model R-24B, and thin layer chromatography (TLC) was usually carried out on Analtech (TM), 250 μm, glass-backed, silica gel GF$_{254}$ slides using a 15% 2-butanone/benzene moving media. MP's are uncorrected.

EXAMPLE 1
(Z)-2,7,β-TRIMETHYL-6-ACETOXY-5-BENZOFURANACRYLIC ACID (E-113) AND SALT THEREOF

Potassium hydroxide (86.6%, 13.62 g, 210.24 mmoles) was dissolved in 800 ml 95% ethanol. Then 4,5',8-trimethylpsoralen(I) (8.0 g, 35.04 mmoles) was added. This mixture was refluxed for thirty minutes while covered with foil. After fifteen minutes all of (I) had dissolved. The solution was cooled to room temperature in an ice-plus-water bath. Then triethylamine (351 ml, 2.53 moles) was added, followed by acetic anhydride (59.6 ml, 631.2 mmoles), with stirring for thirty minutes. The green solution was concentrated to dryness on a rotary evaporator. To this basic gum was added 340 ml of 5% aqueous hydrochloric acid to give a white precipitate. This precipitate was filtered out, washed with two portions of water, then dried in a vacuum oven (80° C., 1 mmHg) to give 9.186 g (31.8 mmoles, 91%) of a white compound. TLC of this compound alongside the starting material (I) revealed two major spots of Rf 0.54 and Rf 0.74 (In benzene:2-butanone;1:1). The spot at Rf 0.74 was observed to be I (TMP). This crude product (9.186 g, 31.8 mmoles) was taken up in chloroform, and extracted sixteen times with 100 ml-portions of 5% aqueous sodium bicarbonate at zero degrees C. Each aqueous layer was immediately acidified with 5 N aqueous hydrochloric acid. The white precipitate which formed was filtered out, washed with two portions of water, and dried to constant weight in a vacuum oven (80° C., 1 mmHG) to give 5.491 g (19.05 mmoles, 56%). TLC of this product in the aforementioned eluent gave one major spot at Rf 0.54 with no visible impurities under short or long-wave ultra-violet light. This partially purified product (5.491 g, 19.05 mmoles) was recrystallized in benzene:ligroin (EKP 513), 85 ml:45 ml. The square white crystals were washed twice with ligroin and dried to constant weight as in the foregoing, to give 4.997 g (17.33 mmoles, 91%) which melted in a range of 199.0°–200.5° C. NMP(CDCl$_3$) δ2.25 (12, methyl groups), δ5.90 (s,1, vinyl), δ6.24 (s,1,furan ring), δ6.98 (s,1,benzene ring), δ9.15 (s,1,carboxylic proton).

Anal.Calcd.for C$_{16}$H$_{16}$O$_5$:C,66.64%; H,5.60%. Found: C,66.41%; H,5.70%.

4,5',8-Trimethylpsoralen.

A solution of (Z)-2,7,β-trimethyl-6-acetoxy-5-benzofuranacrylic acid (100 mg, 0.347 mmol) in 5% aq. NaOH (3.2 mL, 4 mmol) was diluted to 5 mL with water and heated on a steam bath. The first product formed was the sodium salt, which was not isolated. After two minutes, a precipitate appeared. Heating was allowed to continue for one hour before the mixture was poured into a mixture of conc. HCl and ice. The precipitate was collected by filtration, washed with 5% aq. NaOH followed by water, and dried at 80° C./1 mm Hg to obtain a white solid (71.7 mg, 91%), mp 229°–230° C. (alone or mixed with an authentic sample). Its TLC behavior, using benzene:2-butanone::17:3, was identical to that of authentic trimethylpsoralen (Trisoralen-TM).

EXAMPLE 2
cis-7-METHYL-6-ACETOXY-5-BENZOFURANACRYLIC ACID (E-139)

Potassium hydroxide (86.6%, 1.944 g, 30.0 mmol), was dissolved in 50 mL of 95% ethanol, and 8-methylpsoralen (0.50 g, 2.5 mmol) was added. The mixture, covered with foil, was heated to the boiling point. All of the 8-methylpsoralen dissolved. After refluxing for fifteen minutes, the solution was cooled to room temperature in ice-water. Triethylamine (25.04 mL, 180.0 mmol), followed by acetic anhydride (3.54 mL, 37.5 mmol), was added and the yellow-green solution was stirred for thirty minutes, concentrated on the rotary evaporator to a gum, and acidified with conc.HCl and ice. No precipitate formed, so the acidic solution was extracted twice with 50 mL portions of CHCl$_3$, which were combined and extracted with three 100 mL portions of 10% NaHCO$_3$ (aq), pre-chilled to 5° C. The aqueous layers were immediately acidified with conc.HCl and ice. The first portion yielded a precipitate which was collected by filtration, washed with water, and dried (80° C./1 mm), to obtain a colorless solid (0.44 g, 1.69 mmol, 68%), mp 116.5°–117° C. A thin layer chromatogram using benzene:2-butanone::17:3 showed one spot of $R_f \approx 0.5$. The crude product (0.290 g, 1.11 mmol) was recrystallized from CCl$_4$ (5 ml) to obtain an analytical sample (0.174 g, 0.666 mmol, 41%), mp 119.5°–120° C. NMR(CDCl$_3$) δ2.25 (s,6,CH$_3$'s), 5.90 (d,1,J=11 Hz,H—C—COOH), 6.58 (d,1,J=2.4 Hz, C$_3$H), 7.00 (d,1,J=Hz, H—C≡C—COOH), 7.44 (s,1,C$_4$H and d,1,J=2.4 Hz, C$_2$H), 11.06 (s,1, COOH).

Anal. Calcd. for C$_{14}$H$_{12}$O$_5$: C, 64.61; H, 4.65. Found: C,64.06; H,4.65.

EXAMPLE 3
cis-3-METHYL-6-ACETOXY-5-BENZOFURANACRYLIC ACID AND ITS ETHYL ESTER (E-140)

Potassium hydroxide (12.03 g, 85%, 182 mmol) was dissolved in 95% EtOH (300 mL). To this solution was added 4'-methylpsoralen (3.08 g, 15.37 mmol). The reaction container was covered with aluminum foil to keep out light and the mixture was stirred with an overhead stirrer and heated under reflux for fifteen minutes, forming an orange solution. The solution was rapidly cooled to room temperature in an ice-water bath and triethylamine (154 mL, 1.11 mol), followed by Ac$_2$O (22 ml., 235 mmol), was added. The resulting solution was stirred for thirty minutes, initially in an ice bath and then at room temperature, and was then evaporated in vacuo to obtain an orange gum (basic), which was acidified with 5% aqueous hydrochloric acid (ca. 500 mL). A tan precipitate was extracted into CHCl$_3$ (3×250 mL) and the extracts were combined and extracted with saturated aq. NaHCO$_3$ (3×250 mL) and ice. Each chilled NaHCO$_3$ extract was rapidly acidified with conc. HCl and ice (pH 2). The first two NaHCO$_3$ extracts yielded a white precipitate, which was collected by suction filtration, washed with water (3×150 mL) and dried to obtain cis-3-methyl-6-acetoxy-5-benzofuranacrylic acid (3.024 g, 76% yield), mp 115°–118.8° C. In another run, recrystallization from benzene-ligroin gave an analytical sample, mp 109.4°–109.9° C. NMR (CDCl$_3$); δ2.17 (d,3H,J=1.2 Hz, C$_3$CH$_3$); 2.28 (s,3H,OOCCH$_3$); 5.89 (d,1H,J=12 Hz, C$_\alpha$H); 6.92 (d,1H,J=12 Hz, C$_\beta$H); 7.13 (s,1H, C$_7$H); 7.32 (d,1H,J=1.2 Hz, C$_2$H); 7.62 (s,1H,C$_4$H); 10.02 (s,1H, COOH).

Anal. Calcd. for C$_{14}$H$_{12}$O$_5$: C, 64.61; H, 4.65. Found: C,64.82; H,4.40.

Esterification of the title compound with acetic anhydride or acetylchloride is productive of the compound cis-3-methyl-6-acetoxy-5-benzofuranacrylic acid ethyl ester.

EXAMPLE 4
cis-3,7-DIMETHYL-6-ACETOXY-5-BENZOFURANACRYLIC ACID (E-138), SALTS AND 6-ALKANOYLOXY VARIATION Potassium hydroxide (14.100 g, 85% 218 mmol) was dissolved in 95% EtOH (300 mL) and the resulting solution was heated to reflux. The reaction container was covered with aluminum foil. Heat was momentarily removed from the solution and 4',8-dimethylpsoralen (mp 131°–133° C., 3.9 g, 182 mmol) was added, followed by 95% EtOH (100 mL). The dark solution was refluxed for fifteen minutes and rapidly cooled to room temperature in an ice-water bath. Triethylamine (181 mL, 1.31 mol), followed by acetic anhydride (Ac$_2$0) (26 mL, 270 mmol) was added and the solution was stirred for thirty minutes, initially in an ice bath and then at room temperature. The solution was concentrated in vacuo to a red viscous liquid, which was acidified with five percent aqueous hydrochloric acid (ca. 450 mL), and extracted with CHCl$_3$ (3×250 mL). The CHCl$_3$ extracts were combined and extracted with saturated aq. NaHCO$_3$ (4×250 mL) and ice. Each chilled aq. NaCHO$_3$ extract was rapidly acidified with conc. HCl and ice (pH 2). The first three NaHCO$_3$ extracts yielded gummy orange precipitates which were collected using CHCl$_3$ (450 mL), dried (MgSO$_4$), and evaporated in vacuo to obtain crude cis-3,7-dimethyl-6-acetoxy-5-benzofuranacrylic acid (3.558 g, 71% yield). Recrystallization from benzene gave pure cis-3,7-dimethyl-6-acetoxy-5-benzofuranacrylic acid (2.765 g, 78% recovery, 56% yield), mp 158°–160° C. A second recrystallization gave an analytical sample. NMR (CDCl$_3$): δ2.10 (d,3H,J=1.2 Hz, C$_3$CH$_3$); 2.28 (two unresolved singlets, 6H, C$_7$CH$_3$, OOC—CH$_3$); 5.84 (d,1H, J=12 Hz, C$_\alpha$H); 6.90 (d,1H,J=12 Hz, C$_\beta$H); 7.30 (d,1H,J=1.2 Hz, C$_2$H); 7.47 (s,1H,C$_4$H); 10.10 (s,1H,COOH).

Anal. Calcd. for C$_{15}$H$_{14}$O$_5$: C,65.69; H, 5.15. Found: C,65.73; H, 5.43.

By treatment using sodium, potassium, or calcium hydroxide, the title compound is converted into the respective cis-3,7-dimethyl-6-acetoxy-5-benzofuranacrylic acid sodium, potassium, and calcium salts. Upon further treatment with base, these compounds revert via ring reclosure to the starting 4',8-dimethylpsoralen.

Also, employment of propionic anhydride instead of acetic anhydride in the process of the foregoing Example is productive of the 6-propionoxy compound. Introduction into the reaction mixture in the same manner of different alkanoyl esterifying agents is productive of additional 3,7-dimethyl-6-alkanoyloxy-5-benzofuranacrylic acid compounds having varying alkanolyloxy substituents at the 6 position.

EXAMPLE 5
β,3-DIMETHYL-6-ACETOXY-5-BENZOFURANACRYLIC ACID

In the same manner, according to the foregoing Examples, but starting from 4,4'-dimethylpsoralen (mp 220°–221° C.), the title compound is produced.

EXAMPLE 6
4-METHYL-6-ACETOXY-5-BENZOFURANACRYLIC ACID

In the same manner, as given in the foregoing Examples, but starting with 5-methylpsoralen (Capiole and Bareggi, Gazz. Chimica Italiana 98, 444–457 (1968), the title compound is produced.

EXAMPLE 7
α,β,3-TRIMETHYL-6-ACETOXY-5-BENZOFURANACRYLIC ACID

In the same manner, as given in the foregoing Examples, but starting with 3,4,4'-trimethylpsoralen, the title compound is produced.

EXAMPLE 8
β,3,7-TRIMETHYL-6-ACETOXY-5-BENZOFURANACRYLIC ACID

In the same manner given in the foregoing Examples, but starting from 4,4',8-trimethylpsoralen (mp 180°-182° C.), the title compound is produced.

EXAMPLE 9
β-METHYL-3-PROPYL-6-ACETOXY-5-BENZOFURANACRYLIC ACID

In the same manner, as given in the foregoing Examples, but starting from 4'-methyl-4-propylpsoralen (mp 143°-144° C.), the title compound is produced.

EXAMPLE 10
β,3-DIETHYL-6-ACETOXY-5-BENZOFURANACRYLIC ACID

In the same manner, according to the foregoing Examples, but starting from 4,4'-diethylpsoralen, the title compound is produced.

EXAMPLE 11
β,2-DIETHYL-6-ACETOXY-5-BENZOFURANACRYLIC ACID

In the same manner, as given in the foregoing Examples, but starting with 4,5'-diethylpsoralen, the title compound is produced.

EXAMPLE 12
3,7-DIETHYL-6-ACETOXY-5-BENZOFURANACRYLIC ACID

In the same manner given in the foregoing Examples, but starting from 4',8-diethylpsoralen, the title compound is produced.

In the same manner as given in the foregoing, other variations in selection of starting materials are productive of still other loweralkyl-6-loweralkanoyloxy-5-benzofuranacrylic acids and derivatives thereof within the scope of the invention in which one, two, or all of the loweralkyl groups present in the compound are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like. Likewise, "loweralkanoyloxy" comprehends such groups containing two through eight carbon atoms, preferably one through four carbon atoms, such as acetoxy, propionyloxy, butyroyloxy, valeroyloxy, octanoyloxy, and the like.

PHARMACOLOGY

The biophotosensitization activity of the compounds of the present invention was determined by visual grading of erythemal response according to a modification of the procedure of Pathak and Fitzpatrick, J. Invest. Dermatol. 32, 509-518 (1959), entitled "Bioassay of Natural and Synthetic Furocoumarins (Psoralens)". The psoralens are of course "linear" isomers of the furocoumarin family. According to this bioassay of photosensitizing potency, erythema production on albino guinea pig skin is measured visually and the response accorded a gradation definition according to a 0, ±, 1, 2, 3, and 4 scale. The modification employed involved variation of the time between administration of the test compound and exposure to ultraviolet light, thereby enabling measurement of times of onset and decline of the induced photosensitivity effect.

PROTOCOLS

Topical:

Each drug is tested topically at a concentration of one percent (1%) in ethanolic solution. Test sites of one square centimeter of skin each receive one-tenth milliliter of a particular selected test solution thirty minutes prior to exposure to a preselected number of joules of ultraviolet "A" radiation. Three animals of fifteen in each group of guinea pigs are tested with each product to arrive at an average response designated "Reaction Intensity" which is determined by observation and grading 24 hours and 48 hours after administration.

Oral:

Each drug is tested orally by administering a dosage of forty (40) mgm/kgm of body weight to groups of fifteen guinea pigs. The appropriate dosage for each animal is packed into a gelatin capsule and placed far back in the animal's pharynx. Swallowing is assisted by syringe delivery of three milliliters of water. The animals are not allowed to eat or drink six hours before and after administration of each product. The exposure to ultraviolet "A" radiation is at a preselected number of joules per square centimeter at different times after administration, e.g., 10, 20, 30, 45, 60, 90, 120, 180, 240 and 360 minutes after administration. Readings and evaluations are carried out 48 hours post ingestion. When a particular product is exceptionally active in the test, the per os dosage may of course be halved, halved again, or otherwise reduced.

Gradation:

Responses are graded as follows:

0 No response; ± faint erythema; 1+ erythema; 2+ erythema and slight edema; 3+ erythema and intense edema; and 4+ vesiculobullous reaction.

RESULTS

The compounds of the invention show some erythematic topical activity as read at both 24 and 48 hours. They show oral activity as read at 48 hours. The various activities of the various compounds of the invention do, however, vary in intensity from compound to compound. Illustratively, the compounds E-113, 138, 139, and 140 were tested according to the foregoing protocols. The compound E-113 was subjected to three (3) joules of UVA radiation in the topical test, and 1.2 joules in the oral test. The compounds E-138, 139 and 140 were subjected to two (2) joules UVA radiation in the topical test and to two (2) joules of UVA radiation in the oral test. The compound E-139 was so active that testing was continued at the halved dosage and then at the rehalved oral dose of only ten (10) mg/kg. It was clearly superior to the compound 4'-aminomethyl-4,5',8-trimethylpsoralen at all dosages tested orally, both from the standpoint of maximum intensity and duration of intensity. It was also superior from the standpoint of earlier onset, at 40 mg/kg reaching erythema and slight edema after only ten (10) minutes (the evaluation of course being 48 hours post-ingestion). The compound E-113 topically showed a 1+ and a 2+ topical reading at 24 and 48 hours, respectively, and oral readings of 2+ at 20 minutes and 3+ at 30 minutes, 3+ at 45 minutes, 3+ at 60 minutes, 2+ at 90 minutes, and 1+ at 120 minutes. The compound E-138 showed faint erythema at 24 hours, erythema at 48 hours, both in the topical test, and erythema at both 60 minutes and 90 minutes, erythema plus slight edema at 120 minutes, and erythema at 180 and 240 minutes in the oral test.

The compound E-140 showed faint erythema after 24 hours and erythema after 48 hours in the topical test, as well as erythema at 60, 90 and 120 minutes in the oral test. The compound E-139 showed erythema at 24 hours and erythema plus intense edema after 48 hours in the topical test at 40 mg/kg. In the oral test, it showed a 2+ rating at 10 minutes, a 3+ rating at 20 minutes, a 4+ rating at 30 minutes through 240 minutes, and a 3+ rating at 360 minutes. At 20 mg/kg, orally, it showed a 2+ rating at 10 minutes, a 3+ rating at 20 minutes, a 4+ rating at 30 minutes through 180 minutes, a 3+ rating at 240 minutes, and a 2+ rating at 360 minutes. Even at the 10 mg/kg dose, orally, the compound E-139 showed a 2+ rating at 10 through 30 minutes, a 3+ rating at 45 minutes, a 4+ rating at 60 through 120 minutes, a 3+ rating at 180 minutes, and a 1+ rating at 240 minutes.

In contrast, 5'-aminoethyl-4'-methylpsoralen and 8-aminomethylpsoralen show essentially no photosensitizing response orally, although they exhibit 1+ and 1 to 2+ topical responses at 24 and 48 hours. The compounds of the invention show no oral toxicity, no animals dying at any of the dosage levels tested. Also in contrast, the compound 4'-aminomethyl-4,5',8-trimethylpsoralen, although extremely active orally, also shows a high order of oral toxicity, a large number of the animals receiving 40 mgm/kgm thereof dying during the period of their observation, the LD50 for that particular compound apparently being much less than this dosage level.

COMPOSITIONS AND ADDITIONAL UTILITY

This biophotosensitization activity of the compounds of the invention is substantial in the erythemal response test according to the procedure of Pathak and Fitzpatrick, J. Invest. Dermatol., 32, 509–518 (1959), entitled "Bioassay of Natural and Synthetic Furocoumarins (Psoralens)", and usually employed standard modifications thereof, as reported hereinbefore. As "biophotosensitization activity" is employed herein, however, as well as "photochemical sensitivity on the skin of a mammal", and "photosensitizing" or "photosensitization", as well as "photochemotherapy", the compounds of the invention are also active biophotosensitizing agents from another standpoint, inasmuch as they produce functional addition in the standard tests for DNA photoreactivity. See for example, Science 1977, 197 (4306), 906–908; J. Mol. Biol, 1977, 116(4), 661–679; Biochemistry 1977, 16 (6), 1058–1064, and related publications. The compounds are thus clearly useful in the further study of reactions and secondary structures of nucleic acids, and as inhibitors of RNA replication, and are indicated for employment in the inactivation of viruses as well as in the photochemotherapy of psoriasis by the PUVA procedure, in which they are found to be equally as effective as numerous previously-employed psoralen compounds. Their effectiveness is of course dependent upon numerous factors, such as amount of irradiation employed, dosage of the photosensitizing agent, mode of employment (whether topical or oral), and individual skin sensitivities of the mammal subjected to the PUVA therapy, including of course human beings, with respect to which psoriasis is a unique malady. The compounds are accordingly useful for all of the foregoing purposes, but particularly for effecting photochemical sensitivity on the skin of a mammal, these terms as employed herein not being restricted to the production of erythema thereon. They are effective both orally and topically, and the method of effecting photochemical sensitivity on the skin of a mammal merely comprises the step of orally or topically administering to the said mammal an effective photosensitizing dose of a compound of the invention. When the subject is then exposed to ultraviolet radiation, more particularly ultraviolet "A", in the non-burning range, functional adducts are formed with DNA and psoriasis is mitigated in human patients, as aforesaid. Other uses of the compounds of the present invention are also set forth in the foregoing.

The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference may again be made to U.S. Pat. Nos. 4,124,598 and 4,130,568 for representative examples and disclosure concerning the same. The procedure for preparation of such compositions is totally conventional in the art. For oral treatment of psoriasis, the active ingredient is generally formulated in tablets or in gelatin capsules. In such case the diluent may, if desired, be eliminated, although it is generally present. For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg. to about 50 mg. per kg. of body weight, with a dose in the neighborhood of about 5–10 mg. per kg. generally being preferred. Such administration and selection of dosage and unit dosage will of course have to be determined according to established medical principles and under the supervision of the physician in charge of the PUVA therapy concerned. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carrier of types already mentioned.

It is to be understood that the invention is not to be limited to the exact details of operation or exact compounds, compositions, methods, or procedures shown and described, as obvious modifications and equivalents will be apparent to one skilled in the art.

I claim:

1. A compound selected from the group consisting of
   (a) alpha-R-beta-R-2-R-3-R-4-R-7-R-6-loweralkanoyloxy-5-benzofuranacrylic acid, wherein R in each of the stated positions is independently selected from hydrogen and loweralkyl,
   (b) alkali and alkaline earth metal salts thereof, and
   (c) loweralkyl esters thereof.

2. A compound selected from the group consisting of alpha-R-beta-R-2-R-3-R-4-R-7-R-6-loweralkanoyloxy- 5-benzofuranacrylic acid, wherein R in each of the stated positions is independently selected from hydrogen and loweralkyl.

3. A compound selected from the group consisting of alpha-R-beta-R-2-R-3-R-4-R7-R-6-acetoxy-5-benzofuranacrylic acid, wherein R in each of the stated positions is independently selected from hydrogen and methyl.

4. A compound selected from the group consisting of beta-R-2-R-3-R-7-R-6-acetoxy-5-benzofuranacrylic acid, wherein R in each of the stated positions is independently selected from hydrogen and methyl, at least one of said 2, 3, and 7 R substituents being methyl.

5. A compound of claim 1 which is (Z)-2,7,$\beta$-trimethyl-6-acetoxy-5-benzofuranacrylic acid.

6. A compound of claim 1 which is cis-7-methyl-6-acetoxy-5-benzofuranacrylic acid.

7. A compound of claim 1 which is cis-3-methyl-6-acetoxy-5-benzofuranacrylic acid.

8. A compound of claim 1 which is cis-3,7-dimethyl-6-acetoxy-5-benzofuranacrylic acid.

9. A pharmaceutical composition suitable for use in effecting photochemical sensitivity on the skin of a mammal comprising an effective amount of a compound of claim 1 and a pharmaceutically-acceptable carrier or diluent.

10. A pharmaceutical composition suitable for use in effecting photochemical sensitivity on the skin of a mammal comprising an effective amount of a compound of claim 4 and a pharmaceutically-acceptable carrier or diluent.

11. The composition of claim 10 wherein the compound is (Z)-2,7,$\beta$-trimethyl-6-acetoxy-5-benzofuranacrylic acid.

12. The composition of claim 10 wherein the compound is cis-7-methyl-6-acetoxy-5-benzofuranacrylic acid.

13. The composition of claim 10 wherein the compound is cis-3-methyl-6-acetoxy-5-benzofuranacrylic acid.

14. The composition of claim 10 wherein the compound is cis-3,7-dimethyl-6-acetoxy-5-benzofuranacrylic acid.

15. The method of effecting photochemical sensitivity on the skin of a mammal comprising the step of orally or topically administering to the said mammal an effective photosensitizing dose of a compound of claim 1.

16. The method of effecting photochemical sensitivity on the skin of a mammal comprising the step of orally or topically administering to the said mammal an effective photosensitizing does of a compound of claim 4.

17. The method of claim 16 wherein the compound is (Z)-2,7,$\beta$-trimethyl-6-acetoxy-5-benzofuranacrylic acid.

18. The method of claim 16 wherein the compound is cis-7-methyl-6-acetoxy-5-benzofuranacrylic acid.

19. The method of claim 16 wherein the compound is cis-3-methyl-6-acetoxy-5-benzofuranacrylic acid.

20. The method of claim 16 wherein the compound is cis-3,7-dimethyl-6-acetoxy-5-benzofuranacrylic acid.

* * * * *

UNITED STATES PATENT AND TRADEMARK OFFICE
CERTIFICATE OF CORRECTION

PATENT NO. : 4,279,922
DATED : July 21, 1981
INVENTOR(S) : Kurt D. Kaufman

It is certified that error appears in the above—identified patent and that said Letters Patent is hereby corrected as shown below:

Col. 6, line 43; "alkanolyloxy" should read -- alkanoyloxy --
Col. 12, line 21; "does" should read -- dose --

Signed and Sealed this

Ninth Day of February 1982

[SEAL]

Attest:

GERALD J. MOSSINGHOFF

*Attesting Officer*     *Commissioner of Patents and Trademarks*